US00PP30397P2

(12) United States Plant Patent
Miyazaki

(10) Patent No.: US PP30,397 P2
(45) Date of Patent: Apr. 16, 2019

(54) *PETUNIA* PLANT NAMED 'SURF GONITOMI'

(50) Latin Name: ***Petunia* x *hybrida***
Varietal Denomination: Surf Gonitomi

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/732,935

(22) Filed: Jan. 12, 2018

(51) Int. Cl.
*A01H 5/02* (2018.01)

(52) U.S. Cl.
USPC ..... Plt./356.13

(58) Field of Classification Search
USPC ..... Plt./356.13, 356.21, 356.23
CPC ..... A01H 5/02; A01H 5/00; A01H 6/824
See application file for complete search history.

(56) References Cited

U.S. PATENT DOCUMENTS

PP25,121 P2 * 11/2014 Miedema-Jorna ..... A01H 5/02
Plt./356.13

* cited by examiner

*Primary Examiner* — June Hwu
(74) *Attorney, Agent, or Firm* — C. A. Whealy

(57) ABSTRACT

A new and distinct cultivar of *Petunia* plant named 'Surf Gonitomi', characterized by its semi-spreading and mounding plant habit; vigorous growth habit; freely branching habit; freely flowering habit; long flowering period; medium-sized flowers that are bright red purple and white in color; and good garden performance.

1 Drawing Sheet

Botanical designation: *Petunia* x *hybrida*.
Cultivar denomination: 'SURF GONITOMI'.

BACKGROUND OF THE INVENTION

The present invention relates to a new and distinct cultivar of *Petunia* plant, botanically known as *Petunia* x *hybrida* and hereinafter referred to by the name 'Surf Gonitomi'.

The new *Petunia* plant is a product of a planned breeding program conducted by the Inventor in Higashiomi, Shiga, Japan. The objective of the breeding program is to create new semi-spreading, mounding and freely-flowering *Petunia* plants with medium-sized attractive flowers.

The new *Petunia* plant originated from a cross-pollination made by the Inventor in July, 2013 in Higashiomi, Shiga, Japan of a proprietary selection of *Petunia* x *hybrida* identified as code designation PV555-5, not patented, as the female, or seed, parent with a proprietary selection of *Petunia* x *hybrida* identified as code designation 13CV-7, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in July, 2014.

Asexual reproduction of the new *Petunia* plant by terminal vegetative cuttings in a controlled greenhouse environment in Higashiomi, Shiga, Japan since January, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Surf Gonitomi'. These characteristics in combination distinguish 'Surf Gonitomi' as a new and distinct *Petunia* plant:

1. Semi-spreading and mounding plant habit.
2. Vigorous growth habit.
3. Freely branching habit.
4. Freely flowering habit.
5. Long flowering period.
6. Medium-sized flowers that are bright red purple and white in color.
7. Good garden performance.

Plants of the new *Petunia* can be compared to plants of the female parent selection. Plants of the new *Petunia* differ primarily from plants of the female parent selection in flower color as plants of the female parent selection have light salmon pink-colored flowers.

Plants of the new *Petunia* can be compared to plants of the male parent selection. Plants of the new *Petunia* differ primarily from plants of the male parent selection in growth habit as plants of the new *Petunia* are more vigorous than and not as compact as plants of the male parent selection.

Plants of the new *Petunia* can also be compared to plants of the *Petunia* x *hybrida* 'USTUN69002', disclosed in U.S. Plant Pat. No. 27,727. In side-by-side comparisons, plants of the new *Petunia* and 'USTUN69002' differ primarily in the following characteristics:

1. Plants of the new *Petunia* are not as compact as plants of 'USTUN69002'.
2. Plants of the new *Petunia* flower earlier than plants of 'USTUN69002'.

3. Plants of the new *Petunia* have larger flowers than plants of 'USTUN69002'.
4. Plants of the new *Petunia* and 'USTUN69002' differ in flower color as plants of 'USTUN69002' have lavender pink-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Surf Gonitomi' grown in a container.

The photograph at the bottom of the sheet is a close-up view of a typical flowering plant of 'Surf Gonitomi'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and description were taken. In the following description, color references are made to The Royal Horticultural Society Colour Chart, 2015 Edition, except where general terms of ordinary dictionary significance are used.

Botanical classification: *Petunia* x *hybrida* 'Surf Gonitomi'.

Parentage:

*Female, or seed, parent*.—Proprietary selection of *Petunia* x *hybrida* identified as code designation PV555-5, not patented.

*Male, or pollen, parent*.—Proprietary selection of *Petunia* x *hybrida* identified as code designation 13CV-7, not patented.

Propagation:

*Type*.—By terminal vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Semi-spreading and mounding plant habit; freely branching habit with numerous lateral branches developing per plant; pinching enhances lateral branch development; vigorous growth habit.

*Plant height*.—About 30 cm.

*Plant diameter*.—About 90 cm.

Lateral branch description:

*Length*.—About 40 cm to 45 cm.

*Diameter*.—About 6.3 mm.

*Internode length*.—About 1.7 cm.

*Strength*.—Strong, flexible.

*Aspect*.—Mostly outwardly.

*Texture*.—Pubescent.

*Color*.—Close to 144B.

Leaf description:

*Quantity and arrangement*.—About 19 leaves per lateral branch; alternate, simple.

*Length*.—About 3.7 cm.

*Width*.—About 2.8 cm.

*Shape*.—Ovate.

*Apex*.—Broadly acute.

*Base*.—Attenuate.

*Margin*.—Entire; undulate.

*Texture, upper and lower surfaces*.—Pubescent, rough; viscid.

*Venation pattern*.—Pinnate; reticulate.

*Color*.—Developing leaves, upper surface: Close to 137B. Developing leaves, lower surface: Close to 146A. Fully expanded leaves, upper surface: Close to 146A; venation, close to 145A. Fully expanded leaves, lower surface: Close to 146B; venation, close to 145B.

*Petioles*.—Length: About 3.3 mm. Diameter: About 3.4 mm. Texture, upper and lower surfaces: Pubescent. Color, upper and lower surfaces: Close to 145A.

Flower description:

*Flower arrangement and habit*.—Medium-sized single-type salverform flowers arising from upper leaf axils; freely flowering habit with usually about eight to ten flowers developing per lateral branch and about 400 flowers developing per plant during the flowering season; flowers face mostly upright to outwardly.

*Fragrance*.—None detected.

*Natural flowering season*.—Early flowering habit; plants of the new *Petunia* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower buds*.—Length: About 4.2 cm. Diameter: About 8.3 mm. Shape: Cylindrical. Color: Close to 145C; towards the apex, close to 182D; developing petals, close to 70B to 70C.

*Flower diameter*.—About 5.8 cm.

*Flower tube length*.—About 2.75 cm.

*Flower tube diameter, proximally*.—About 2.5 mm.

*Flower tube diameter, distally*.—About 1.2 cm.

*Corolla*.—Quantity and arrangement: Five in a single whorl, fused at the base and opening into a flared trumpet. Petal length from throat: About 2.6 cm. Petal width: About 3 cm. Petal shape: Roughly spatulate. Petal apex: Cuspidate to rounded. Petal margin: Entire; slightly lobed; slightly undulate. Petal texture, upper and lower surfaces: Smooth, glabrous; velvety. Throat texture: Smooth, glabrous. Tube texture: Pubescent. Color: Petal, when opening, upper surface: Distally, close to 46C fading proximally to close to 54D and NN155A. Petal, when opening, lower surface: Distally, close to 54C fading proximally to close to 54D. Petal, fully opened, upper surface: Distally, close to 58C fading proximally to close to 65D and N155B; main veins, close to 152D and lateral veins, close to 52A; colors do not change with development. Petal, fully opened, lower surface: Distally, close to 54B fading proximally to close to 55B and N155D; venation, similar to lamina colors; colors do not change with development. Throat: Distally, close to 155B; proximally, close to 145D; main veins, close to N144A and lateral veins, close to 182A. Tube: Distally, close to N155D; center, close to NN155A; proximally, close to 157D; venation, similar to lamina colors.

*Calyx*.—Arrangement: One star-shaped calyx tube with five sepals arranged in a single whorl and fused at the base. Sepal length: About 1 cm. Sepal width: About 2.7 mm. Sepal shape: Lanceolate. Sepal apex: Acute. Sepal margin: Entire. Sepal texture, upper and lower surfaces: Pubescent; viscid. Color, upper surface: Close to 137B. Color, lower surface: Close to 146A.

*Peduncles*.—Length: About 1.4 cm. Diameter: About 1.6 mm. Strength: Strong, flexible. Aspect: Upright to outwardly. Texture: Pubescent. Color: Distally, close to 144B; proximally, close to 144A.

*Reproductive organs*.—Stamens: Quantity per flower: Five. Filament length: About 1.9 cm. Filament color: Close to NN155B. Anther shape: Ellipsoidal. Anther size: About 2.2 mm by 1.2 mm. Anther color: Close to 8D. Pollen amount: Abundant. Pollen color: Close to 2D. Pistils: Quantity per flower: One. Pistil length: About 2.4 cm. Style color: Close to 145D. Stigma shape: Transversely ellipsoidal. Stigma color: Close to 144C. Ovary color: Close to 144A. Seeds and fruits: Seed and fruit development have not been observed on plants of the new *Petunia* to date.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants to date.

It is claimed:

1. A new and distinct *Petunia* plant named 'Surf Gonitomi' as illustrated and described.

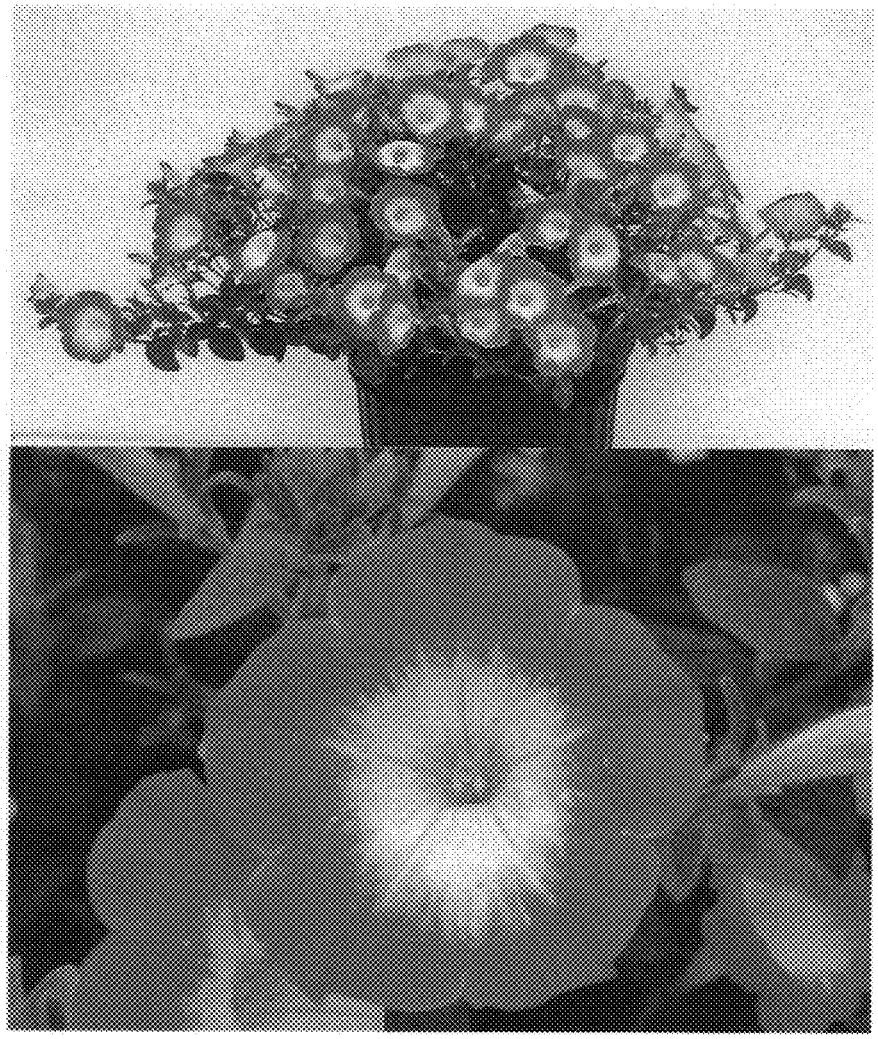

* * * * *